(12) United States Patent
Goebel et al.

(10) Patent No.: US 7,739,060 B2
(45) Date of Patent: Jun. 15, 2010

(54) DETECTION SYSTEM AND USER INTERFACE FOR A FLOW CYTOMETER SYSTEM

(75) Inventors: Clement James Goebel, Ypsilanti, MI (US); Collin A. Rich, Ypsilanti, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 103 days.

(21) Appl. No.: 11/963,384

(22) Filed: Dec. 21, 2007

(65) Prior Publication Data

US 2008/0215297 A1 Sep. 4, 2008

Related U.S. Application Data

(60) Provisional application No. 60/871,616, filed on Dec. 22, 2006.

(51) Int. Cl.
*G06F 17/40* (2006.01)
*G06F 17/00* (2006.01)

(52) U.S. Cl. .............................. 702/45; 702/21; 702/32; 250/459.1; 73/863.21

(58) Field of Classification Search .................. 702/45, 702/21, 32
See application file for complete search history.

(56) References Cited

U.S. PATENT DOCUMENTS

| | | | | |
|---|---|---|---|---|
| 5,204,884 A | * | 4/1993 | Leary et al. | 377/10 |
| 5,308,990 A | * | 5/1994 | Takahashi et al. | 250/459.1 |
| 5,367,474 A | * | 11/1994 | Auer et al. | 702/21 |
| 5,469,375 A | * | 11/1995 | Kosaka | 702/77 |
| 5,684,480 A | | 11/1997 | Jansson | |
| 6,115,085 A | | 9/2000 | George et al. | |
| 6,809,804 B1 | * | 10/2004 | Yount et al. | 356/73 |
| 7,024,316 B1 | * | 4/2006 | Ellison et al. | 702/45 |
| 7,105,355 B2 | | 9/2006 | Kurabayashi et al. | |
| 7,106,442 B2 | | 9/2006 | Silcott et al. | |
| 2002/0097392 A1 | | 7/2002 | Minneman et al. | |
| 2003/0054558 A1 | | 3/2003 | Kurabayashi et al. | |
| 2003/0223061 A1 | | 12/2003 | Sebok et al. | |
| 2006/0219873 A1 | * | 10/2006 | Martin et al. | 250/214 R |
| 2008/0228444 A1 | * | 9/2008 | Olson et al. | 702/189 |

* cited by examiner

*Primary Examiner*—Hal D Wachsman
(74) *Attorney, Agent, or Firm*—Jeffrey Schox

(57) ABSTRACT

The detection system of the first preferred embodiment includes a detector, having a wide dynamic range, that receives photonic inputs from the interrogation zone and produces an analog signal; and an analog-to-digital converter (ADC), having a high bit resolution, that is coupled to the detector and converts an analog signal to a digital signal. The digital signal includes an initial data set of the full dynamic range of the input signals from the flow cytometer sample. The method of extracting and analyzing data from a flow cytometer system of the first preferred embodiment preferably includes the steps of: collecting a full dynamic range of input signals from a flow cytometer sample; recognizing and annotating aggregate particle events; and storing an initial data set and an annotated data set of the full dynamic range of the input signals from the flow cytometer sample.

19 Claims, 2 Drawing Sheets

DETECTION SYSTEM AND USER INTERFACE FOR A FLOW CYTOMETER SYSTEM

CROSS-REFERENCE TO RELATED APPLICATIONS

This application claims the benefit of U.S. Provisional Application No. 60/871,616, filed 22 Dec. 2006, which is incorporated in its entirety by this reference.

TECHNICAL FIELD

The present invention relates generally to the field of flow cytometers, and more particularly to detection systems and user interfaces in the field of flow cytometers.

BACKGROUND

One common problem in flow cytometry is the necessity for coincidence detection in the presence of multiple particles that are closely spaced or joined in the sample. These closely spaced or joined particles are know as "doublets" when two particles are together or "higher-order aggregate particles" when three or more particles are together. Users of flow cytometry systems typically want to know if the sample contains aggregate particles. Depending on the experiment, aggregate particles can either be undesirable (such as contaminants from poor sample preparation) or desirable (such as cells in the process of cell division/mitosis).

Conventional flow cytometry systems operate with a user interface that may include a doublet discrimination module (DDM) feature. When this feature is activated, the detection system can detect closely spaced or joined particles, known in the art as "doublets", via an algorithm that can recognize the characteristic "peak-trough-peak" waveform produced by doublets. When a doublet event is detected, the DDM artificially increases at least one of the parameter values to help the user more easily visualize and gate these events. This modification is not desirable, however, because the data is not preserved exactly as it was originally generated.

The limitations of the detection system and user interface of typical flow cytometer systems with a DDM feature have at least two disadvantages: (1) the potential loss of valuable original data because the DDM artificially increases at least one of the parameter values, modifying the data at the time of acquisition; and (2) the inability to observe and "undo" changes made to the data by the DDM without running additional samples.

Accordingly, there is a need in the art to create a new and improved detection system and user interface for a flow cytometer that avoids or minimizes these disadvantages. The present invention provides such new and improved detection system for a flow cytometer.

DESCRIPTION OF THE PREFERRED EMBODIMENT

The following description of the preferred embodiment of the invention is not intended to limit the invention to this preferred embodiment, but rather to enable any person skilled in the art of flow cytometers to make and use this invention.

Figure 1:
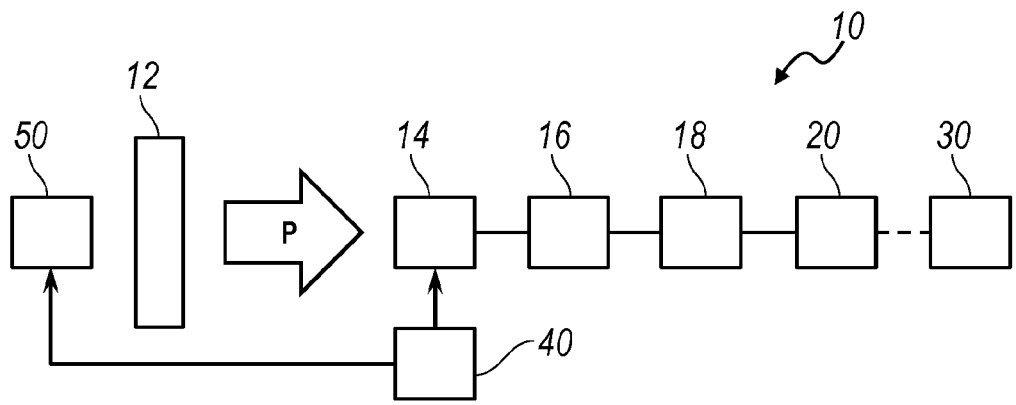
FIG. 1 is a schematic block diagram of a flow cytometer detection system in accordance with a first preferred embodiment of the present invention.
Figure 2:
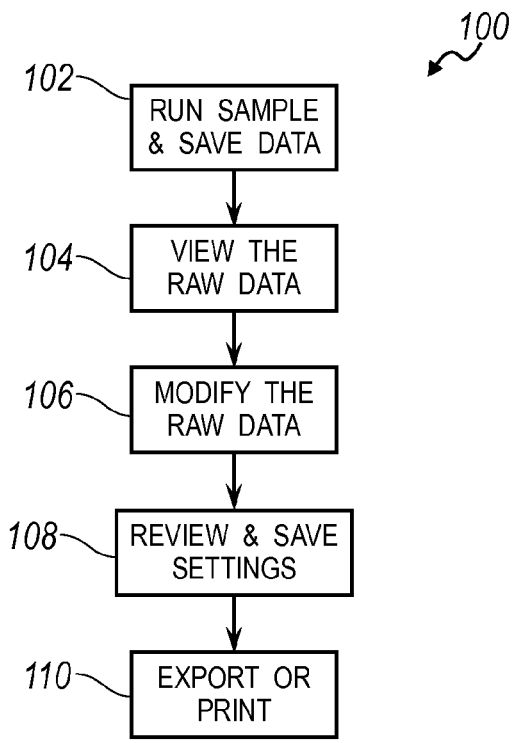
FIGS. 2 and 3 are schematic block diagrams of a flow cytometer user interface in accordance with the preferred embodiment of the present invention.

As shown in FIGS. 1 and 2, the preferred embodiment of the invention includes a detection system 10 adapted to recognize and annotate aggregate particle events, and a user interface system 100 adapted to identify, isolate, display, and/or analyze data including the annotated higher-order aggregate particle events.

1. Detection System

As shown in FIG. 1, the detection system 10 of the first preferred embodiment is preferably designed to be integrated into a flow cytometer having an interrogation zone 12. The detection system 10 of the first preferred embodiment allows for the recognition and annotation of doublets or higher-order aggregate particle events. The present invention makes it possible to preserve the measurements as they were detected and to annotate the aggregate particle events for later visualization or isolation for analysis. The detection system 10 has sufficient data capacity to process additional parameters such as one that annotates each event as either an aggregate particle event or a non-aggregate particle event. The detection system 10 also includes an algorithm (implemented through hardware or software) that is able to recognize the characteristic "peak-trough-peak" waveform produced by aggregate particle events and annotate the events accordingly.

The detection system 10 includes a detector 14 adapted to receive photonic inputs P from the interrogation zone 12 and produce an analog signal, and an analog-to-digital converter (ADC) 20 coupled to the detector 14 and adapted to convert an analog signal to a digital signal. The detector 14 has a dynamic range and the ADC 20 has a high bit resolution such that the detection system 10 has sufficient data capacity to process additional parameters including one that recognizes and annotates aggregate particle events.

The detector 14 of the preferred embodiment functions to receive photonic inputs from the interrogation zone and produce analog signals based on these photonic inputs. The detector 14 is preferably operable over a wide dynamic range. As used herein, the term "wide dynamic range" is preferably defined as greater than or equal to 100 dB. The detector 14 preferably has a luminous sensitivity between 80 and 120 microamps per lumen, but may alternatively have a luminous sensitivity of any suitable value. The detector 14 is preferably operable over a spectral range of approximately 400 to 700 nanometers, but may alternatively be operable over any suitable spectral range. Preferably, the detector 14 includes one or more PIN photodiodes and a synchronous detection unit (not shown). The PIN photodiodes function to receive photonic inputs P from an interrogation zone 12, and convert the impending electromagnetic radiation into an electrical signal. Although a PIN photodiode is preferred, the detector 14 may use other suitable detection devices with a wide dynamic range, such as specialized photomultipliers or other photodiodes. The synchronous detection unit functions to provide the fidelity for the input signals in the lower end of the signal range. The synchronous detection unit is preferably similar to the synchronous detection unit disclosed in U.S. Pat. No. 7,105,355 entitled "Flow Cytometers and Detection System of Lesser Size", which is incorporated in its entirety by this reference. Although this synchronous detection unit is preferred, the detector 14 may use other suitable signal conditioners. Further, in certain circumstances, the detector 14 may omit the synchronous detection unit, which would yield a circuit with wide dynamic range, but less luminous sensitivity.

The detection system 10 of the preferred embodiment further includes an amplifier 16 that is coupled to the detector 14. The amplifier 16 preferably receives the electrical signal of the detector 14 and amplifies the signal by a predetermined amount, depending upon the strength of the output and the breadth of the detector range. Alternatively, the amplifier 16 may include variable attenuators such that the amplifier 16 applies a dynamically variable gain to the signal. Although the amplifier 16 preferably operates in the electrical domain, the amplifier 16 may alternatively operate in the optical domain. For example, the amplifier 16 may be integrated or partially integrated into the detector 14, such as in the case of an avalanche photodiode (APD), which is an amplified photodetector known in the art. The preferred amplifier 16 has a signal-to-noise ratio (SNR) ranging between approximately 100 dB and 120 dB.

The detection system 10 of the first preferred embodiment also includes an automatic gain control (AGC) unit 40. The AGC unit 40 is preferably coupled to both an exciter 50 and the amplifier 16. Alternatively, the AGC unit 40 may be coupled to either the exciter 50 or the amplifier 16. Operating on the amplifier 16, the AGC unit 40 functions to dynamically vary the gain of the amplifier 16 with respect to the analog signal produced by the detector 14. This dynamic gain control allows a single detector 14 with limited dynamic range to track an input signal with much larger dynamic range. Operating on the exciter 50, the AGC unit 40 functions to dynamically vary the output of the exciter 50, thereby varying the signal excited in the interrogation zone 12 and by extension the optical properties of the photonic inputs P. The AGC unit 40 further functions to keep the generated signal within the dynamic range of the detector 14. The AGC unit 40 may be integrated into the amplifier 16, the exciter 50, or both. Alternatively, the AGC unit may be remotely coupled to the amplifier 16, the exciter 50 or both.

The detection system 10 of the first preferred embodiment further includes a compression unit 18 that is coupled to the amplifier 16. The compression unit 18 functions to reduce the dynamic range of the plurality of electrical signals from the amplifier 16 and compress that data into an electrical signal with a smaller dynamic range that is appropriate for the ADC 20 of the preferred system. In the preferred embodiment, the detection system 10 incorporates signal compression to obtain better resolution for the input signals in the lower end of the signal range. The compression unit 18 preferably uses a nonlinear compression algorithm, such as a logarithmic compression algorithm, but may use a linear, parametric, or any other suitable approach. In alternative embodiments, the detection system 10 may omit the compression unit 18.

The ADC 20 of the detection system 10 functions to convert an analog signal into a digital signal that is readily usable by a digital circuit, processor, or computing device. The ADC 20 preferably includes a high bit resolution. As used herein, the term "high bit resolution" is preferably defined as greater than or equal to 16-bits, and more preferably defined as greater than or equal to 24-bits. The ADC 20 preferably includes a Signal-to-Noise Ratio (SNR) of approximately greater than 100 dB, but may alternatively include a SNR of any suitable value.

The detection system 10 of the preferred embodiment preferably interfaces with an analysis engine 30, which functions to apply gain and scaling factors to the acquired data, independent of the acquisition step. The analysis engine 30 also includes an algorithm that is able to recognize aggregate particle events and annotate them throughout the acquisition step. The algorithm preferably recognizes the characteristic "peak-trough-peak" waveform produced by aggregate particle events and annotates the events accordingly while simultaneously preserving the raw, unmodified data. The algorithm may additionally or alternatively recognize other characteristic aspects, such as a unique width versus height or area for the waveform. Each event is preferably labeled as either an "aggregate particle event" or "doublet" or a "non-aggregate particle event", but may alternatively be labeled in any other suitable fashion such as labeling the number of aggregate particles, labeling a descriptor of the separation between the two particles (such as 20% conjoined or "loosely connected") based on the peak versus trough ratios, labeling if the aggregate particle is a contaminant, or labeling if the aggregate particle is a cell undergoing cell division or mitosis.

The analysis engine 30 may be configured as a software and/or hardware module. In an alternative variation, the detection system 10 and the analysis engine 30 may be physically separated. That is, the detection system 10 might store raw, collected data (with aggregate particle events annotated) on a memory device (such as a CD-ROM or other such media), which can then be removed and/or transferred to the analysis engine 30 (such as a PC) for analysis. This approach has the advantage of minimizing the use time by each user of the detection system 10. The collection of the data in this manner eliminates the expenditure of valuable user time during the pre-set step and avoids the potential loss of valuable data.

2. User Interface

As shown in FIG. 2, the user interface 100 of the preferred embodiment of the invention extracts data from the full dynamic range of a flow cytometer in a single run and annotates specific events (such as doublets or higher-order aggregate particle events) across the full dynamic range, and then manipulates scaling and/or culling factors and allows for the identification, isolation, and/or analysis of the annotated events across the full dynamic range after the data have been collected. The data of the full dynamic range are collected and stored in raw or unmodified form during the acquisition step with the aggregate particle events identified and then the user interface can display the unmodified data and/or modified data. Because scaling and/or culling factors can be applied and the identification, isolation, and/or analysis of the annotated events can be completed after the acquisition step is complete, the user interface facilitates real-time comparisons between the raw and modified data on a single, unique sample run. This additionally allows for the reversible discrimination of aggregate particle events at any point in the analysis of the collected, labeled data. Scaling and/or culling and the identification, isolation, and/or analysis of the annotated events can be adjusted or undone without the need to re-run pilot samples, which saves time, reduces the amount of sample required, and eliminates the potential of lost data due to incorrect gain settings or identification, isolation, and/or analysis of the annotated events.

As shown in FIG. 2, the flow cytometer user interface of the preferred embodiment includes the steps of (a) running the sample and saving all collected data (102), (b) viewing the raw (or "unmodified") data (104), (c) modifying the raw data (106) (e.g., scaling and/or culling the raw data), (d) reviewing and saving the modified settings (108), and (e) exporting the saved data (110). Once the sample has been run and all collected data have been saved, the user can repeat the steps of modifying the raw data, saving the modified settings, and exporting the saved data as many times as necessary or desirable without the need to run an additional sample.

Figure 3:
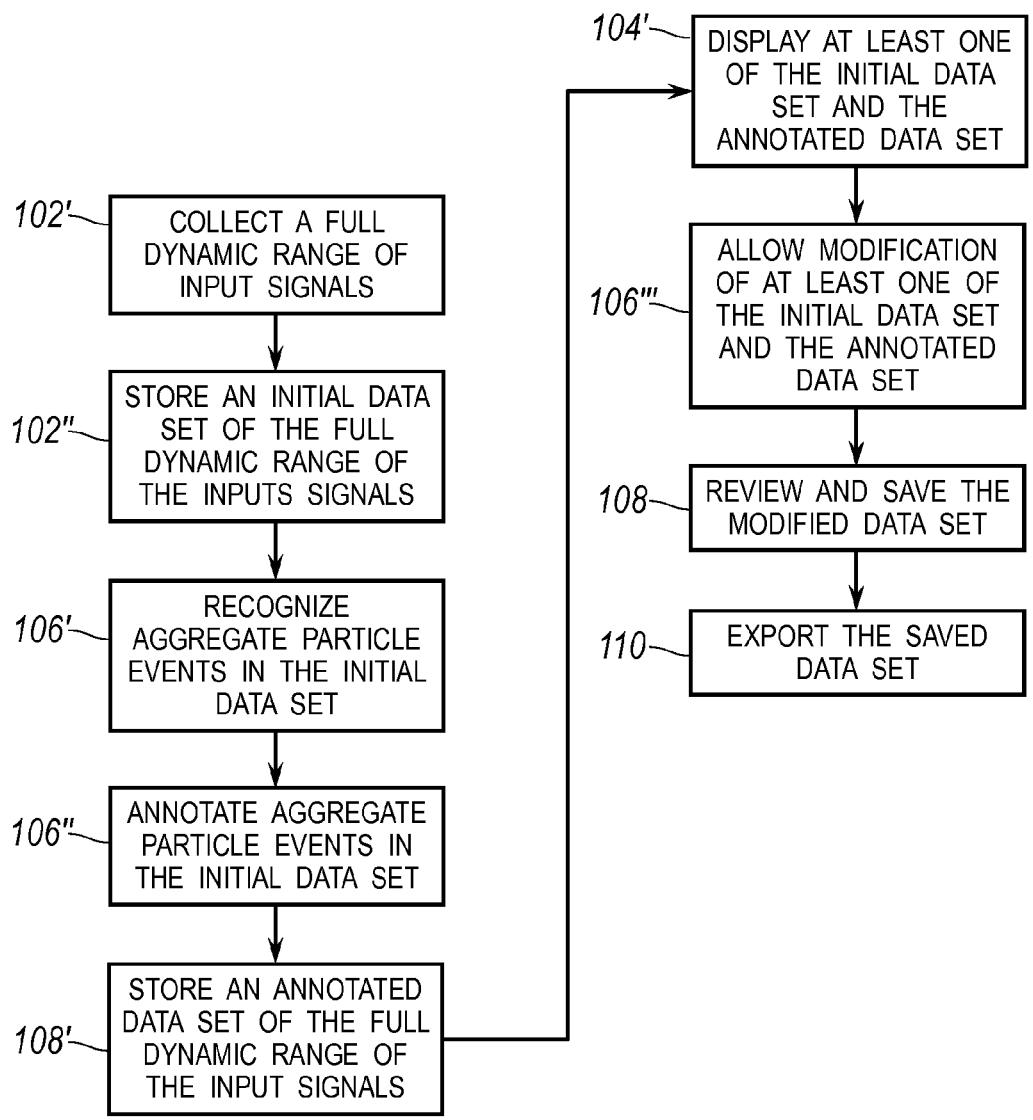

As shown in FIG. 3, the flow cytometer user interface of the preferred embodiment includes the steps of collecting a full dynamic range of input signals from a flow cytometer sample (102'), storing an initial data set of the full dynamic range of the input signals from the flow cytometer sample (102"), recognizing aggregate particle events in the initial data set (106'), annotating aggregate particle events in the initial data set (106"), storing an annotated data set of the full dynamic range of the input signals from the flow cytometer sample (108'), and displaying at least one of the initial data set and the annotated data set (104'). The step of recognizing aggregate particle events in the initial data set preferably occurs substantially simultaneously with collecting a full dynamic range of input signals from a flow cytometer sample. The flow cytometer user interface of the preferred embodiment further includes the steps of allowing modification of at least one of the initial data set and the annotated data set (106'''), reviewing and saving the modified data set (108), and exporting the saved data set (110).

The user interface of the preferred embodiment is coupled to the detection system 10 of the preferred embodiment, but may alternatively be coupled to any suitable diagnostic and/or analysis system. In an alternative embodiment, the user interface is in electronic communication with a composite of several narrow dynamic range flow cytometers.

In the preferred embodiment, the first step of 'running the sample and saving all collected data' (102) includes the collection (i.e., acquisition) and electronic storage of the full dynamic range of input signals (in raw, unmodified format) from a flow cytometer sample with the aggregate particle events recorded with annotation such that they can be identified and/or culled from the other event data for the purposes of analysis and display. The full dynamic range of input signals is preferably defined as the range of input signals that provides a 1:100,000 ratio, and more preferably a 1:1,000,000 ratio, between the faintest objects and the brightest objects. The full dynamic range of input signals is preferably captured by a 24 bit process, which translates to roughly 16,700,000 levels of information, but may alternatively be captured by any suitable process. Preferably, the captured data includes an error rate induced by electric noise of less than one-percent. In the preferred embodiment, the data are collected in a raw, unmodified format without the use of, or the adjustment in, the gain level of the detector. The collection of the data in this manner eliminates the expenditure of valuable user time and avoids the potential loss of valuable data through misconfiguration of the system.

The data collected in the first step, includes the information collected from the algorithm that is able to recognize aggregate particle events and annotate them. The algorithm recognizes the characteristic "peak-trough-peak" waveform produced by aggregate particle events (or another unique aspect of the waveform) and annotates the events accordingly, creating an annotated data set, while simultaneously preserving the raw, unmodified data (the initial data set). Each event is preferably labeled as either an "aggregate particle event" or "doublet" or a "non-aggregate particle event", but may alternatively be labeled in any other suitable fashion such as labeling the number of aggregate particles, labeling a descriptor of the separation between the two particles (such as 20% conjoined or "loosely connected") based on the peak versus trough ratios, labeling if the aggregate particle is a contaminant, or labeling if the aggregate particle is a cell undergoing cell division or mitosis. This labeling information is collected and stored along with the full dynamic range of input signals (in raw, unmodified format) from a flow cytometer sample.

The second step of 'viewing the raw data' (104) permits the user to observe the raw data and annotated data that has been collected and stored from the sample run and identify the anticipated appropriate modifications for the sample and the possible identification, isolation, and/or analysis of the annotated events. In the preferred embodiment, the user interface presents the raw data after the acquisition is complete. In an alternative embodiment, the user interface presents the raw data during the acquisition step. In a first "local" variation of the preferred embodiment, the original, raw data set to be viewed is acquired from a flow cytometer coupled to the user interface; in a second "remote" variation, the original data set is acquired from an electronic storage medium. When the user interface is coupled to a broad dynamic range flow cytometer, as in the preferred embodiment, the user interface can display data from greater than four decades of signal.

The third step of 'modifying the raw data' (106) permits the user to manipulate (e.g. scale and/or cull) the data collected across the full dynamic range of input signals from the flow cytometer sample and to identify, isolate, and/or analyze the annotated events. In this step, the user interface permits the user to perform real-time comparisons between the raw and modified data on a single, unique sample run. Additionally, scaling and/or culling and the identification, isolation, and/or analysis of the annotated events can be adjusted or undone without the need to re-run pilot samples allowing multiple adjustments on the same initial data set.

In the preferred embodiment, the user scales, culls, isolates, and/or analyzes the raw data to select a subset of signals and/or aggregate particle events that correspond to the desired sample population. The user is permitted to apply gain and scaling factors to the acquired data or perform any other suitable analysis in order to review the occurrence and the features of the aggregate particle events. This is performed independently of the acquisition step and permits the user to adjust the bounds of the data and analyze the data. In an alternative embodiment, the user interface automatically scales and/or culls the raw data and performs an analysis on the annotated data based on an appropriate algorithm. In this alternative embodiment, the user interface may accept a user command that corresponds to, or identifies, the desired sample population. The modifying of raw data preferably occurs after data acquisition is complete, and multiple signal gain/scaling adjustments can be made on a single, unique data set.

The user interface of the preferred embodiment may be virtual, physical, or any suitable combination. In the virtual variation, the knobs, sliders, and other controls are shown only on a display and not in a physical unit. The controls, whether virtual or physical, permit the single, unique data set to be modified in a step-wise, sequential fashion. Alternatively, the user interface may permit the single, unique data to be repeatedly or iteratively modified. Scaling is preferably applied hierarchically based on forward scatter, which can be expanded to include any or all of the available data channels (scatter and fluorescent) in a progressive fashion. Scaling may, however, be applied in any suitable manner.

Any number of subsets of data can be generated that correspond to one or more sample populations contained within the raw data set. Preferably, the user interface permits each subset (i.e. modification) of the raw data and the settings used to generate the desired subset of data to be individually saved, recorded, and identified. Alternatively, the user interface may permit subsets of raw data that are generated by sequential or iterative modifications and the settings used to generate the desired subset of data to be saved and identified at each iteration and in their totality.

In the preferred embodiment, the user interface utilizes one or more graphical, menu-driven formats that can accept and display data sets, such as those from a flow cytometer with broad dynamic range. In an alternative embodiment, the user interface utilizes a numerical display format. The user interface permits the modification of its display representation through the application of scaling and/or culling factors to the original data set or through the analysis of data sets to include, exclude, and/or combine data based on the annotated aggregate particle events. In a first variation, the user interface simultaneously presents modified and raw representations of a single data set. In a second variation, the user interface simultaneously presents multiple data sets that can be simultaneously viewed, compared, and analyzed. The user can undo or otherwise alter the modifications of one or more data sets using the menu-driven options.

The user interface of the preferred embodiment represents raw data and modified data using any suitable format, including graphically and numerically. The user interface enables observation of the consequences of scaling, culling, or analysis modifications on a unique data set by simultaneous representation of raw and modified data. For example, aggregate particle events can be displayed in plots as a unique color or can be "scrubbed" (or removed) from the data set for statistical analysis of non-aggregate particle events. In one variation, separate graphs are generated from the raw and modified data and are displayed in separate frames, which preferably represents a preview of the export/print version of the viewed data. In an alternative variation, the raw and modified data are superimposed on one another in the same graph frame, with each data set preferably distinguished by color and/or shading. In yet another variation, the consequences of each modification applied to the raw data in the generation of the modified data are represented in independent planes of the same graph frame, and all modifications can be superposed.

The fourth step of 'reviewing and saving the modified settings' (108) permits the user to identify the modifications made to the original data set and to store the setting(s) used to generate the desired subset of data, thus allowing the user to save both the data and the corresponding scaling, culling, and/or analysis parameters. The user interface provides virtual instrument settings that can be adjusted, which generate a corresponding subset of data from the raw (i.e. original) data set. The user can repeat the steps of modifying the raw data and saving the desired subset of data and modified settings as many times as necessary and/or desirable, without the need for running additional sample through the flow cytometer. If the user generates the subset of data by making one or more alterations in the virtual settings, the user can access the previously saved alterations made to the subset of data and retrace or "undo" the alterations sequentially. In the preferred embodiment, the user interface will prompt the user to save the modified subset of data, the settings used to generate the data, and any other pertinent information regarding the sample or data acquisition; in an alternative embodiment, the data settings are saved automatically. The user interface can apply hierarchical scaling factors to independent data channels (e.g. scatter channels and fluorescent channels).

The fifth step of 'exporting the saved data' (110) permits the user to transfer the original (raw) data set and/or the modified subset of data from the flow cytometer system to a different medium, such as a printout or an electronic file. The data may be transferred to any suitable medium for subsequent viewing, analysis, and/or storage, and the settings used to generate the data and other pertinent information regarding the sample or data acquisition may also be included.

The flow cytometer user interface of the preferred embodiment may further include the step of acting upon the information previously generated. In one version, the flow cytometer user interface may automatically chose whether or not to sort a particular cell based on whether it is a doublet. In another version, the flow cytometer user interface may automatically signal to the user upon the occurrence (or omission) of a particular number of "aggregate particle events" during a particular time period, or upon a particular rise or drop in the ratio of "aggregate particle events" to "non-aggregate particle events". The flow cytometer user interface may, of course, perform or initial any suitable action based on any suitable measurement or parameter derived from the use of the flow cytometer user interface.

As a person skilled in the art of flow cytometry will recognize from the previous detailed description and from the figures and claims, modifications and changes can be made to the preferred embodiment of the invention without departing from the scope of this invention defined in the following claims.

We claim:

1. A detection system for a flow cytometer having an interrogation zone through which a flow cytometer sample passes, comprising:
 a detector that receives photonic inputs from the interrogation zone and produces an analog signal, the detector having a wide dynamic range;
 an analog-to-digital converter (ADC), coupled to the detector, that converts an analog signal to a digital signal, the ADC having a high bit resolution;
 wherein the digital signal includes an initial data set of the full dynamic range of the input signals from the flow cytometer sample; and
 an analysis engine that recognizes aggregate particle events in the initial data set and annotates the recognized aggregate particle events, thereby creating an annotated data set of the full dynamic range of the input signals from the flow cytometer sample.

2. The detection system of claim 1 wherein the analysis engine recognizes a "peak-trough-peak" waveform produced by aggregate particle events and annotates the recognized aggregate particle events, thereby creating an annotated data set of the full dynamic range of the input signals from the flow cytometer sample.

3. The detection system of claim 2 wherein the analysis engine labels an aggregate particle event as an "aggregate particle event" and a non-aggregate particle event as a "non-aggregate particle event".

4. The detection system of claim 1 wherein the high bit resolution of the ADC is defined as greater than or equal to 16-bits.

5. The detection system of claim 1 wherein the wide dynamic range of the detector is defined as greater than or equal to 100 dB.

6. A method of extracting and analyzing data from a flow cytometer system comprising the steps of:
 collecting a full dynamic range of input signals from a flow cytometer sample;
 storing an initial data set of the full dynamic range of the input signals from the flow cytometer sample;
 recognizing aggregate particle events in the initial data set with use of an algorithm;
 annotating aggregate particle events in the initial data set to create an annotated data set of the full dynamic range of the input signals from the flow cytometer sample;
 storing the annotated data set; and
 displaying at least one of the initial data set and the annotated data set.

7. The method of claim 6 wherein recognizing aggregate particle events in the initial data set occurs substantially simultaneously with collecting a full dynamic range of input signals from a flow cytometer sample.

8. The method of claim 6 wherein recognizing aggregate particle events in the initial data set includes identifying a "peak-trough-peak" waveform produced by aggregate particle events.

9. The method of claim 8 wherein annotating aggregate particle events in the initial data set includes labeling an aggregate particle event as an "aggregate particle event" and a non-aggregate particle event as a "non-aggregate particle event".

10. The method of claim 9 wherein annotating aggregate particle events in the initial data set includes further labeling an aggregate particle event with the number of aggregate particles in the event.

11. The method of claim 6 further comprising the steps of:
allowing modification of at least one of the initial data set and the annotated data set;
saving the modified data set; and
exporting the saved data set.

12. The method of claim 11 wherein displaying at least one of the initial data set and the annotated data set includes permitting a user to observe at least one of the initial data set and the annotated data set from the full dynamic range of input signals, and permitting the user to identify the appropriate modifications for at least one of the initial data set and the annotated data set.

13. The method of claim 11 wherein allowing modification of at least one of the initial data set and the annotated data set includes permitting a user to manipulate at least one of the initial data set and the annotated data set across the full dynamic range of input signals from the flow cytometer sample and to generate a modified data set.

14. The method of claim 13 wherein allowing modification of at least one of the initial data set and the annotated data set further includes permitting the user to:

perform real-time comparisons between the initial data set, the annotated data set, and the modified data set on a single flow cytometer sample;
adjust or undo modifications, to make multiple adjustments on the same initial data set or annotated data set; and
generate at least one subset of data that corresponds to one or more sample populations contained within at least one of the initial data set and the annotated data set.

15. The method of claim 14 wherein annotating aggregate particle events in the initial data set includes labeling an aggregate particle event as an "aggregate particle event" and a non-aggregate particle event as a "non-aggregate particle event", wherein allowing modification of at least one of the initial data set and the annotated data set further includes permitting the user to:
isolate at least one of the annotated aggregate particle events and the annotated non-aggregate particle events; and
remove the annotated aggregate particle events or the annotated non-aggregate particle events.

16. The method of claim 11 wherein allowing modification of at least one of the initial data set and the annotated data set further includes providing adjustable virtual instrument settings.

17. The method of claim 11 wherein allowing modification of at least one of the initial data set and the annotated data set further includes utilizing a graphical, menu-driven format that accepts and displays data sets.

18. The method of claim 17 wherein utilizing a graphical, menu-driven format includes displaying separate graphs that are generated from the initial data set, the annotated data set, and the modified data set in separate frames.

19. The method of claim 18 wherein aggregate particle events are displayed in a first color and non-aggregate particle events are displayed in a second color.

* * * * *